United States Patent [19]
Aikins et al.

[11] Patent Number: 5,637,692
[45] Date of Patent: *Jun. 10, 1997

[54] AZETIDINONE INTERMEDIATES TO CARBACEPHALOSPORINS AND PROCESS

[75] Inventors: James Aikins; John P. Gardner; Billy G. Jackson; John R. Rizzo; Eddie V. Tao, all of Indianapolis, Ind.

[73] Assignee: Eli Lilly and Company, Indianapolis, Ind.

[*] Notice: The term of this patent shall not extend beyond the expiration date of Pat. No. 5,453,503.

[21] Appl. No.: 464,480

[22] Filed: Jun. 5, 1995

Related U.S. Application Data

[63] Continuation of Ser. No. 104,383, Aug. 9, 1993, Pat. No. 5,453,503, which is a continuation of Ser. No. 958,589, Oct. 7, 1992, abandoned, which is a continuation of Ser. No. 773,745, Oct. 10, 1991, abandoned, which is a continuation of Ser. No. 652,808, Feb. 7, 1991, abandoned, which is a continuation-in-part of Ser. No. 405,602, Sep. 11, 1989, abandoned, which is a continuation-in-part of Ser. No. 256,538, Oct. 11, 1988, abandoned.

[51] Int. Cl.$^6$ ............... C07D 463/00; C07D 205/085; C07B 37/10
[52] U.S. Cl. ............................................. 540/205
[58] Field of Search ............................................. 540/205

[56] References Cited

U.S. PATENT DOCUMENTS 4,665,171  5/1987  Evans et al. ............................. 540/364

FOREIGN PATENT DOCUMENTS 365190  4/1990  European Pat. Off. .

OTHER PUBLICATIONS

Jackson, et al., *Tetrahedron Letters*, 31(44), pp. 6317–6320 (1990), "Synthesis of Carbacephem Antibiotics: Synthesis via Dieckmann Reaction Using Phenyl Esters to Direct the Regioselectivity of the Cyclization."

Hatanaka et al., *Tetrahedron Letters*, 24(44), pp. 4837–4838 (1983), "A Simple Synthesis of (+/–)–1–Carbacephem Derivatives."

Campaigne, et al., *J. Het. Chem.*, 14, 497–503, 1976, "Synthesis of Some 5–Aryl–2,2'–dipyrromethenes as Analogs of Prodigiosin (1)".

Mauger et al., *J. Org. Chemistry*, 42(6), 1000–1005 (1977), "Synthesis and Stereochemistry of 3–Hydroxy–5–methylproline, a New Naturally Occurring Imino Acid".

Blake, et al., *JACS*, 86, 5293–5299 (1964), "Pyrrolidinones by Intramolecular Condensation".

Bonjoch et al., *Tetrahedron*, 40(13), pp.2505–2511 (1984), "Synthesis of 2,5–Piperidinediones. Regioselectivity in the Dieckmann Cyclization$^1$."

Nagao et al., *Chemistry Letters*, 1861–1864 (1987), "A New Finding in the Dieckmann Type Annulation of a Chiral Half–Thiol Diester Having Latent σ–Symmetry."

*Primary Examiner*—Mark L. Berch
*Attorney, Agent, or Firm*—James P. Leeds

[57] ABSTRACT

7β-Amino-3-hydroxy-1-carba(1-dethia)-3-cephem-4-carboxylic acid esters are provided via cyclization of cis-3-(substituted amino)-1-(2-substituted 2-oxoethyl)-4-substituted azetidinones. The 7β-amino-3-hydroxy-1-carba (1-dethia)-3-cephem-4-carboxylic acid esters are useful chiral intermediates to β-lactam antibiotics.

6 Claims, No Drawings

AZETIDINONE INTERMEDIATES TO CARBACEPHALOSPORINS AND PROCESS

CROSS REFERENCE TO RELATED APPLICATION

This application is a continuation, of application Ser. No. 08/104,383, filed on Aug. 9, 1993, U.S. Pat. No. 5,453,503 which is a continuation of application Ser. No. 07/958,589, filed on Oct. 7, 1992, now abandoned, which is a continuation of application Ser. No. 07/773,745 filed on Oct. 10, 1991, now abandoned, which is a continuation of application Ser. No. 07/652,808 filed on Feb. 7, 1991, now abandoned, which is a continuation-in-part of application Ser. No. 07/405,602 filed on Sep. 11, 1989, now abandoned, which is a continuation-in-part of application Ser. No. 07/256,538 filed on Oct. 11, 1988, now abandoned.

BACKGROUND OF THE INVENTION

This invention relates to β-lactam antibiotics. In particular, it relates to intermediates of 1-carba(1-dethia)-3-cephem-4-carboxylic acids, and to a process for preparing certain intermediates to such compounds.

Hashimoto et al. in U.S. Pat. No. 4,335,211 disclose a class of 1-carbacephalosporins having potent oral activity. These compounds are currently being evaluated for the treatment of various conditions such as the common upper- and lower-respiratory tract infections caused by the pathogen H. influenzae. One such compound, known as loracarbef or LY163892, has shown activity against a broad spectrum of bacteria in laboratory tests. Loracarbef has proven to be a relatively stable compound which exhibits high blood levels and a relatively long half-life. Loracarbef is currently being clinically evaluated.

The 1-carbacephalosporins thus far have not been obtained from natural sources, for example, as microbial metabolites. Accordingly, methods for the total synthesis of these promising compounds are highly desirable, particularly methods which are adaptable to large scale manufacture.

SUMMARY OF THE INVENTION

The present invention relates to a process for preparing a compound of the Formula (I)

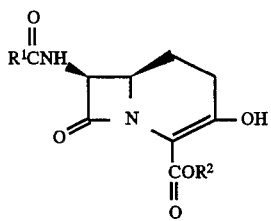

wherein $R^1$ is $C_1$–$C_6$ alkyl; a phenyl group

wherein a and a' independently are hydrogen, $C_1$–$C_4$ alkyl, $C_1$–$C_4$ alkoxy or halogen; a group represented by the formula

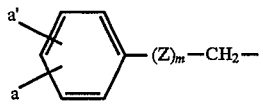

wherein Z is O or S, m is 0 or 1, and a and a' have the same meanings as defined above; or $R^1$ is $R^{1''}$ O wherein $R^{1''}$ represents $C_1$–$C_4$ alkyl, $C_5$–$C_7$ cycloalkyl, benzyl, nitrobenzyl, methoxybenzyl, or halobenzyl; and $R^2$ is a carboxy-protecting group, comprising reacting a compound of the Formula (II)

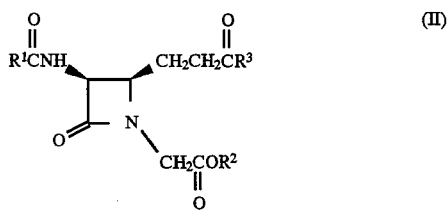

wherein $R^1$ and $R^2$ are as defined above and $R^3$ is a leaving group of the formula —$OR^4$, wherein $R^4$ is $C_1$–$C_6$ alkyl, $C_2$–$C_6$ alkenyl, phenyl, or phenyl substituted with one, two, or three substituents selected from $C_1$–$C_6$ alkylthio, nitro, halo, carboxy, and amido, with a non-nucleophilic strong base.

The present invention also provides an intermediate of the Formula (II)

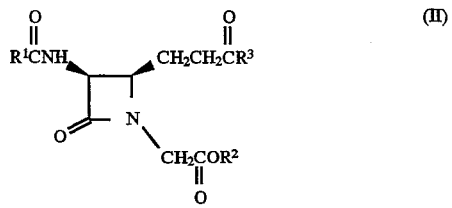

wherein $R^1$, $R^2$ and $R^3$ are as defined above.

The present invention also includes a process for the preparation of a compound of the formula

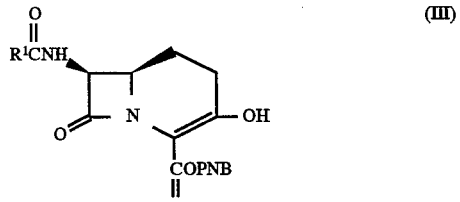

wherein $R^1$ is defined as above, by reacting a compound of the formula IV

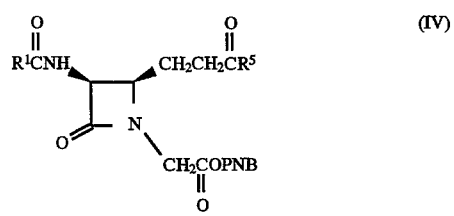

wherein $R^1$ is as defined above and $R^5$ is a leaving group, with a sodium tertiary alkoxide at a temperature of between about −65° C. and about −100° C., or with a lithium tertiary alkoxide at a temperature of between about −25° C. and about room temperature, or about 27° C.

DETAILED DESCRIPTION OF THE INVENTION

A "carboxy-protecting group" refers to a carboxy function bonded to one of the carboxylic acid substituents commonly employed to block or protect the carboxylic acid functionality while reacting other functional groups on the compound. Examples of such carboxylic acid protecting groups include methyl, t-butyl, phenyl, 4-nitrobenzyl, 4-methoxybenzyl, diphenylmethyl, benzyl, 2,4,6-trimethoxybenzyl, trityl, 4-methoxytrityl, 4,4'-dimethoxytrityl, and 4,4',4"-tri-methoxytrityl and like moieties. The species of carboxy-protecting group employed is not critical so long as the derivatized carboxylic acid is stable to the condition of subsequent reaction(s) and can be removed at the appropriate point without disrupting the remainder of the molecule. In particular, neither the protected carboxy function nor the protecting group itself should react with the solvents, reagents, products and other substrate molecules of the process aspect of the invention described below. Similar carboxy-protecting groups such as those described by E. Haslam in "Protective Groups in Organic Chemistry" J. F. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5 are suitable.

A "leaving group", as defined herein, refers to a substituent which is displaced from the molecule during the chemical reaction. Such leaving groups include leaving groups defined by —O—$R^4$ or —$SR^4$ where $R^4$ represents $C_1$–$C_6$ alkyl, $C_2$–$C_6$ alkenyl, phenyl, or phenyl substituted with one, two or three substituents such as $C_1$–$C_6$ alkyl, $C_1$–$C_6$ alkoxy, $C_1$–$C_6$ alkylthio, nitro, halo, carboxy, amido and the like, and related substituents. Preferred $R^4$ groups include phenyl, halophenyl and nitro-phenyl, especially 4-nitrophenyl.

"$C_1$–$C_6$ Alkyl" represents a straight or branched alkyl chain having from one to six carbon atoms. Typical $C_1$–$C_6$ alkyl groups include methyl, ethyl, n-propyl, isopropyl, n-butyl, sec.-butyl, n-pentyl and n-hexyl.

"$C_2$–C6 Alkenyl" represent a straight or branched alkenyl chain having from 2 to 6 carbon atoms. Typical $C_2$–$C_6$ alkenyl groups include vinyl, allyl, 2-butenyl, 3-pentenyl, 2-hexenyl and the like.

While the entire scope of process variables taught herein are believed operable, the present process and intermediates do have preferred aspects. Preferred compounds of the above formula are where $R^1$ is benzyl, phenyl, benzyloxy or methylenephenoxy (wherein m is 1, Z is oxygen and a and a' are both hydrogen) and $R^2$ is alkyl, especially methyl, or substituted benzyl, especially 4-nitrobenzyl and 4-methoxybenzyl. Other preferred aspects of the present invention will be noted hereinafter.

The process of the present invention is carried out by combining at least one, but preferably at least three, molar equivalents of base with the compound of Formula (II) in a mutual organic solvent. More specifically, the process is carried out by first preparing a solution of the base and a suitable solvent. A variety of organic solvents may be used with the aprotic solvents being preferred. Typical aprotic solvents suitable for use in the reaction include the ethers such as 1,2-dimethoxyethane and diethyl ether, and the cyclic ethers, such as tetrahydrofuran (THF), which is preferred. In general, the solvent employed in the present process can be any convenient solvent which solubilizes the azetidinone starting material and which is unreactive with the base employed in the reaction. The amount of solvent used in preparing the solution is not critical, but no more than necessary to dissolve the base need be used.

Non-nucleophilic strong bases are employed in the process of the present invention. Typical non-nucleophilic strong bases include the alkali metal alkoxides of tertiary alcohols such as lithium t-butoxide, potassium t-butoxide, sodium t-butoxide, sodium t-pentoxide, and potassium t-pentoxide, lithium t-pentoxide, and other non-nucleophilic strong bases such as lithium hexamethyldisilazide, and lithium diisopropylamide.

The process of the present invention is preferably carried out under substantially anhydrous conditions. The term "substantially anhydrous conditions", as used herein, represents reaction conditions which are virtually free from water due to the reactivity of the base with water. Accordingly, solvents are preferably dried prior to use in the present invention and the base is kept moisture-free prior to its use. Further, it is preferred that all reaction vessels be thoroughly dried prior to their use, for example by flame or heat drying. It is also preferred that the process be carried out in an inert atmosphere, such as under nitrogen or argon gas.

The solution of base thus prepared is next cooled to a temperature in the range of about 25° C. to about –100° C., more preferably from about –50° C. to about –80° C.

Next, the compound of Formula (II) is combined with the base. Preferably, a solution of the azetidinone of Formula (II) is added to the cold solution of base. Generally, the same solvent used to solubilize the base is used to solubilize the azetidinone, but such is not required.

The reaction is substantially complete within about 10 minutes to 24 hours when conducted at a temperature in the range of about –100° C. to about 25° C. The desired compound is readily isolated by quenching the mixture with acid, such as hydrochloric acid or acetic acid, preferably at a temperature in the range of about –80° C. to about –60° C. Typically, the mixture is then warmed to about 25° C. and a small amount of water added. The desired compound may be isolated by extraction with a water immiscible organic solvent or crystallization by the addition of common solvents and collecting the solid. The isolated residue may be further purified if desired by standard techniques such as crystallization from common solvents or column chromatography over solid supports such as silica gel or alumina. (See, for example U.S. Pat. No. 4,782,144).

As is known in the art, $OR^4$ leaving groups are considered to be less effective leaving groups than —$SR^4$ leaving groups, used by Evans et al. U.S. Pat. No. 4,665,171, and Hatanaka et al., *Tet. Letters*, 24, 4837–4838 (1983). (Greene, *Protective Groups in Organic Synthesis*, p. 180–181, (1981), 2 March, *Advanced Organic Chemistry*, p. 28, p. 325, (1977); Fieser & Fieser, *Advanced Organic Chemistry*, p. 319, (1961); 2 Carey & Sundberg, *Advanced Organic Chemistry*, p. 113, (1988)). Surprisingly, it was determined that the use of —$OR^4$ groups resulted in substantially the same yield as when the —$SR^4$ groups were used. Further, the odor problems associated with the use of thiols is also avoided.

As noted above the 7β-amino-3-hydroxy-1-carba-(1-dethia)-3-cephem-4-carboxylic acid esters prepared by the process of the present invention are valuable intermediates to 1-carbacephalosporin antibiotics, more particularly to 3-halo-1-carba-3-cephem compounds disclosed in U.S. Pat. No. 4,708,956, herein incorporated by reference. The 3-hydroxy-1-carba-cephalosporins are converted to the 3-halo antibiotics according to the process disclosed in U.S. Pat. No. 4,673,737, also herein incorporated by reference. According to this process a 7-(protected amino)-3-hydroxy-1-carbacephalosporin ester is reacted with an acylating reagent which is a derivative of trifluoromethane sulfonic acid, such as trifluoromethanesulfonic anhydride or trifluoromethanesulfonyl chloride, and the like. The resulting 3-trifluoromethylsulfonyloxy-1-carba-3-cephems are reacted with a lithium halide to provide the corresponding 3-halo-1-carbacephalosporin antibiotic.

In forming the compounds of formula III

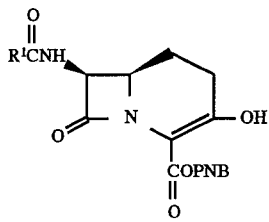   (III)

starting with a compound of the formula IV

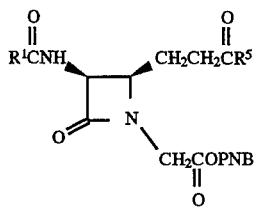   (IV)

it was determined that low yields were provided when potassium butoxide was used at a temperature of between about −65° C. to about −100° C. (see Jackson et al., *Tet. Letters*, Vol. 31, No. 44, pp 6317–6320 (1990), examples 2, 5, 9, 10, and 13). At this temperature range, sodium as the cation (sodium tertiary alkoxide) provided enhanced yields. At a temperature range of between about −25° C. to about room temperature, sodium and potassium tertiary alkoxides provided low yields of formula III, while lithium tertiary alkoxides provided enhanced yields. It is believed that the reactivity of the particular cation (potassium, sodium, lithium) is greatly controlled by temperature, thus resulting in yield differentials between different cations. Further, this phenomenon does not seem to be related to the particular leaving group (—$SR^4$, —$OR^4$) employed.

The cis-3-(substituted amino)-1-(2-substituted 2-oxoethyl)-4-azetidin-2-one propanoic acid esters employed as starting materials in the process of the present invention may be prepared by acylating the amino group of a 3β-amino-4-[2-(2-furyl)-ethyl]azetidin-2-one followed by N-substitution of the azetidinone with a substituted haloacetate. The resulting compound is then ozonolyzed to the 4-carboxyethyl N-alkylated protected aminoazetidinone, which is finally converted to the desired cis-3-(substituted amino)-1-(2-substituted 2-oxoethyl)-4-azetidin-2-one propanoic acid ester. These reactions may be represented by the following scheme:

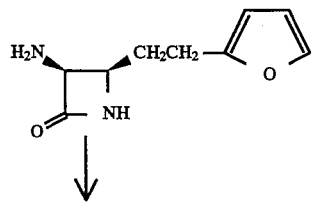

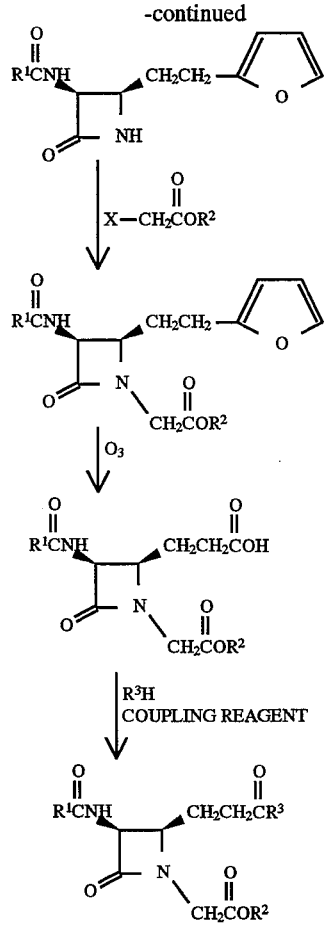

The 3β-amino-4-[2-(2-furyl)ethyl]azetidin-2-one 1 is a known compound readily prepared by prior art processes. For example, Evans et al. in U.S. Pat. No. 4,665,171, herein incorporated by reference, teaches the synthesis of this compound by reducing a 4β-[2-(2-furyl) ethyl]-3β-(4(S)-aryloxazolidin-2-one-3-yl)-1-benzyl-azetidinone with lithium in ammonia in the presence of about three molar equivalents of t-butyl alcohol.

The 3β-(substituted amino)-4-[2-(2-furyl)-ethyl]azetidin-2-one 2 may be prepared by acylating the 3β-amino substituent of the compound of formula 1 under standard acylating conditions.

The 1-(2-substituted 2-oxoethyl)-3β-(substituted amino)-4-[2-(2-furyl)ethyl]azetidin-2-one 3 is prepared by reacting the compound of formula 2 with a substituted haloacetate in the presence of an acid scavenger. Typical substituted haloacetates include substituted bromo- or chloroacetates, whereas commonly used acid scavengers include bases such as sodium hydroxide and related bases.

Ozonolysis of 3 provides the 4-carboxyethyl N-alkylated protected aminoazetidinone 4, which is finally converted to the desired compound of Formula (II) cis-3-(substituted amino)-1-[(2-substituted 2-oxoethyl]-4-azetidin-2-one propanoic acid ester employing an alcohol $R^3H$, wherein $R^3$ is as defined above, and a coupling reagent under standard conditions. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as N-ethoxycarbonyl-2-ethoxy-1,2-dihydro-quinoline (EEDQ). It should be understood that different leaving groups may be used ($R^5$) to result in formation of compounds of formula IV.

The following Examples further illustrate specific aspects of the present invention. The Examples are not intended to be limiting in any respect and should not be so construed. In the following Examples the term "IR" stands for "Infrared Spectrum", "UV" represents "Ultraviolet Spectrum", and "FDMS" represents "Field Desorption Mass Spectrum".

EXAMPLE 1

Synthesis of 7-[[(phenylmethoxy)carbonyl]-amino]-3-hydroxy-8-oxo-1-azabicyclo[4.2.0]oct-2-ene-2-carboxylic acid (4-methoxyphenyl)methyl ester A 50 ml three neck round bottom flask fitted with a nitrogen inlet tube, thermometer, nitrogen outlet tube, addition funnel and magnetic stirrer was charged with 0.39 g (3.5 mmol) of potassium t-butoxide and 15 ml of THF under a nitrogen atmosphere. The resulting solution was cooled to about −78° C. with an external dry ice/acetone bath and a solution of 0.55 g (1.0 mmol) of cis-3-[[(phenylmethoxy) carbonyl]amino]-1-[2-[(4-methoxyphenyl)methoxy]-2-oxoethyl]-4-azetidin-2-one propanoic acid phenyl ester in 5 ml of THF was added dropwise over a period of four minutes. The yellow solution was stirred at about −75° C. for about 30 minutes and 0.29 ml (5.0 mmol) of glacial acetic acid was added. The mixture was allowed to warm to room temperature over a period of ten minutes and 30 ml of water was added. The resulting mixture was extracted with 50 ml of ethyl acetate. The organic layer was separated, dried over anhydrous sodium sulfate and concentrated under vacuum to provide 2.38 g of a solution. To the solution was added 15 ml of diethyl ether followed by 15 ml of hexanes. The mixture was stirred for one hour, and the precipitated solid was collected by vacuum filtration and washed with 10 ml of hexanes: diethyl ether (1:1, v:v). The solid was dried in a vacuum oven at 40° C. to provide 0.32 g of 7-[[ (phenylmethoxy)carbonyl]amino]-3-hydroxy-8-oxo-1-azabicyclo[4.2.0]oct-2-ene-2-carboxylic acid (4-methoxyphenyl)methyl ester as a white solid.

Analysis calculated for $C_{24}H_{24}N_2O_7$
Theory: C, 63.71; H, 5.35; N, 6.19;
Found: C, 63.98; H, 5.51; N, 6.13.
IR ($CHCl_3$): 3439, 1766, 1725, 1663, 1614, 1516, 1387, 1338, 1050 cm$^{-1}$;
UV ($CH_3CH_2OH$): λ max 280 nm (7560), 226 nm (14,600);
FDMS: 452=M+

EXAMPLE 2

Synthesis of 7-(benzoylamino)-3-hydroxy-8-oxo-1-azabicyclo[4.2.0]oct-2-ene-2-carboxylic acid (4-methoxyphenyl)methyl ester A. cis-3-(Benzoylamino)-1-[2-[(4-methoxyphenyl)-methoxy ]-2-oxoethyl]-4-azetidin-2-one propanoic acid (4-nitrophenyl) ester A mixture of 1.5 g (3.42 mmol) of cis-3-(benzoylamino) -1-[2-[(4-methoxyphenyl)methoxy]-2-oxoethyl]-4-azetidin-2-one propanoic acid, 0.81 g (5.1 mmol) of carbonyldiimidazole and 30 ml of dry THF was stirred at room temperature for one hour. To the mixture was added 0.71 g (5.1 mmol) of p-nitrophenol and the resulting mixture was stirred at room temperature overnight. The mixture was concentrated under vacuum and the residue was dissolved in 50 ml of ethyl acetate. The resulting solution was washed with 30 ml of 1N hydrochloric acid, 20 ml of a saturated sodium chloride solution and 50 ml of water. The organic phase was dried over anhydrous magnesium sulfate and concentrated under vacuum to provide 1.72 g of a yellow oil. The oil was chromotographed over silica gel employing hexane/ethyl acetate as the eluant to provide 0.4 g of a white solid following evaporation under vacuum. mp=146° −152° C.

Analysis calculated for $C_{29}H_{27}N_3O_9$
Theory: C, 62.03; H, 4.85; N, 7.48;
Found: C, 62.27; H, 4.92; N, 7.20.

B. A solution of 10 ml of THF and 0.17 g (1.54 mmol) of potassium t-butoxide under a nitrogen atmosphere in a 100 ml three neck round bottom flask was cooled to about −78° C. with an external dry ice/acetone bath. To this solution was added a solution of 0.27 g (0.48 mmol) of cis-3-(benzoylamino)-1-[2-[(4-methoxyphenyl)methoxy]-2-oxoethyl]-4-azetidin-2-one propanoic acid (4-nitrophenyl) ester in 3 ml of dry THF dropwise over a period of about 5 minutes. The resulting yellow solution was stirred for about 50 minutes at about −78° C. and 30 ml of 1N hydrochloric acid, 20 ml of a saturated sodium chloride solution and 50 ml of ethyl acetate were added. The organic layer was separated, washed with water, dried over anhydrous magnesium sulfate and concentrated under vacuum to provide 0.28 g of 7-(benzoylamino)-3-hydroxy-8-oxo-1-azabicyclo [4.2.0]oct-2-ene-2-carboxylic acid (4-methoxyphenyl) methyl ester as an oil.

H-NMR(DMSO): β2.10 (multiplet, 2H); 2.70 (multiplet, 2H); 3.96 (singlet, 3H); 4.07 (multiplet, 1H); 5.49 (singlet, 2H); 5.76 (quartet, 1H); 7.18 and 7.70 (multiplet, 4H); 7.82 and 8.20 (multiplet, 5H); 9.40 (doublet, 1H).

EXAMPLE 3

Synthesis of 7-(benzoylamino)-3-hydroxy-8-oxo-1-azabicyclo[4.2.0]oct-2-ene-2-carboxylic acid (4-methoxyphenyl)methyl ester A. cis-3-(Benzoylamino)-1-[2-[(methoxyphenyl) methoxy]-2-oxoethyl]-4-azetidin-2-one propanoic acid (2,4, 5-trichlorophenyl) ester A mixture of 1.5 g (3.42 mmol) of cis-3-(benzoylamino) -1-[2-[(4-methoxyphenyl)methoxy]-2-oxoethyl]-4-azetidin-2-one propanoic acid, 0.81 g (5.1 mmol) of carbonyldiimidazole and 30 ml of dry THF was stirred at room temperature for two hours. To this mixture was added 1.0 g (5.1 mmol) of 2,4,5-trichlorophenol and the resulting mixture was stirred at room temperature for 19 hours. The mixture was heated to reflux for 30 minutes and stirred for an additional 4½ hours at room temperature. The reaction mixture was concentrated under vacuum, and the residue was dissolved in ethyl acetate. The resulting solution was washed with 1N hydrochlric acid, dried over anhydrous magnesium sulfate and concentrated under vacuum to provide 2.34 g of an oil. The oil was chromatographed over silica gel while eluting with hexane/ethyl acetate to provide 0.46 g of cis-3-(benzoylamino)-1-[2-[(methoxyphenyl) methoxy]-2-oxoethyl]-4-azetidin-2-one propanoic acid (2,4, 5-trichlorophenyl) ester.

Analysis calculated for $C_{29}H_{25}Cl_3N_2O_7$
Theory: C, 56.19; H, 4.07; N, 4.52; Cl, 17.16;
Found: C, 56.12; H, 4.14; N, 4.35; Cl, 16.91.

B.

A 100 ml three neck round bottom flask was charged with 0.27 g (2.37 mmol) of potassium t-butoxide and 15 ml of THF under a nitrogen atmosphere. The resulting solution was cooled to about −78° C. with an external dry ice/acetone bath and a solution of 0.46 g (0.74 mmol) of cis-3-(benzoylamino)-1-[2-[(4-methoxyphenyl)methoxy]-2-oxoethyl]-4-azetidin-2-one propanoic acid (2,4,5- trichlorophenyl)methyl ester in 5 ml of THF was added dropwise. The reaction mixture was stirred for about 210 minutes at about −78° C. and quenched with 30 ml of 1N hydrochloric acid, 20 ml of an aqueous saturated sodium chloride solution and. 50 ml of ethyl acetate. The organic layer was separated, washed with water, dried over anheydrous magnesium sulfate and concentrated under vacuum to provide 0.37 g of an oil containing 7-(benzoylamino)-3-hydroxy-8-oxo-1-azabicyclo[4.2.0]-oct-2-ene-2-carboxylic acid (4-methoxy-phenyl) ester. The identity of the compound was confirmed by thin layer chromatography.

EXAMPLE 4

Synthesis of 7-(benzoylamino)-3-hydroxy-8-oxo-1-azabicyclo[4.2.0]oct-2-ene-2-carboxylic acid (4-methoxyphenyl)methyl ester Fifteen milliliters of THF were added to 0.35 g (3.1 mmol) of potassium t-butoxide under a nitrogen atmosphere in a three neck round bottom flask. The resulting solution was cooled to about −78° C. with an external dry ice/acetone bath and charged with a solution of 0.5 g (0.97 mmol) of cis-3-(benzoylamino)-t-[2-[(4-methoxyphenyl)methoxy]-2-oxoethyl]-4-azetidin-2-one propanoic acid (4-nitrophenyl) ester in 5 ml of THF via syringe. The resulting yellow solution was stirred for about 30 minutes and 0.29 ml (5.0 mmol) of glacial acetic acid was added. The mixture was allowed to warm to room temperature for five minutes and 30 ml of water and 50 ml of ethyl acetate was added. The organic layer was separated, dried over anhydrous magnesium sulfate and concentrated under vacuum to provide 2.2 g of 7-(benzoylamino)-3-hydroxy-8-oxo-1-azabicyclo [4.2.0]-oct-2-ene-2-carboxylic acid (4-methoxyphenyl) methyl ester as an oil. Five milliliters of diethyl ether were added to the oil and the solution was seeded with a crystal of the desired compound. An additional 10 ml of diethyl ether was added and the mixture was stirred for 10 minutes. Next, 10 ml of hexanes was added dropwise over a period of five minutes and the mixture was stirred for one hour at room temperature. The precipitated solid was collected by vacuum filtration, washed with diethyl ether: hexane (3:2, v:v) and dried under vacuum to give 0.30 g of the title compound as off-white crystals. The identity of the compound was confirmed by thin layer chromatography.

EXAMPLE 5

Synthesis of 7-(benzoylamino)-3-hydroxy-8-oxo-1-azabicyclo[4.2.0]oct-2-ene-2-carboxylic acid (4-methoxy-phenyl) methyl ester A 300 ml two neck round bottom flask was charged with 3.35 g (31.2 mmol) of potassium t-butoxide under nitrogen. Tetrahydrofuran (150 ml) was added to the flask and the resulting solution was cooled to about −78° C. with an external dry ice/acetone bath. In a separate container 5.0 g (8.9 mmol) of cis-3-(benzoylamino)-1-[2-[(4-methoxyphenyl)methoxy-2-oxoethyl]-4-azetidin-2-one propanoic acid (4-nitrophenyl) ester was dissolved in 35 ml of THF under nitrogen. The resulting solution was added via syringe to the flask containing the potassium t-butoxide solution over a period of about 10 minutes. The reaction mixture was stirred at −78° C. for about one hour and a thin layer chromatograph employing toluene:ethyl acetate (7:3, v:v) with 1 ml of acetic acid indicated that no starting material remained. The reaction mixture was allowed to warm to about 0° C. and 2.5 ml of glacial acetic acid was added. The mixture was stirred for about 30 minutes and concentrated under vacuum at about 40° C. The resulting oil was dissolved in methylene chloride and the resulting solution was washed five times with 10% by volume aqueous saturated sodium bicarbonate solution, once with water and dried over anhydrous magnesium sulfate. The solution was concentrated under vacuum to dryness to provide 3.47 g of the desired compound as compared by thin layer chromatography to an authentic reference standard.

EXAMPLE 6

Synthesis of 7-[[(phenylmethoxy)carbonyl]amino]-3-hydroxy-8-oxo-1-azabicyclo[4.2.0[oct-2-ene-2-carboxylic acid (4-nitrophenyl)methyl ester A solution of 0.56 g (4.99 mmol) of potassium t-butoxide in 10 ml of dry THF was cooled to about −74° C. with an external dry ice/acetone bath under a nitrogen atmosphere. To the reaction mixture was added a solution of 0.8 g (1.43 mmol) of cis-3-[[(phenylmethoxy)carbonyl]-amino]-1-[2-(4-nitrophenyl)-methoxy-2-oxoethyl ]-4-azetidin-2-one propanoic acid phenyl ester in 10 ml of dry THF dropwise over a period of about 10 minutes. The reaction mixture was stirred at about −70° C. for about 10 minutes and 0.409 ml (7.2 mmol) of glacial acetic acid was added. The reaction mixture was allowed to warm to room temperature with stirring and 50 ml of ethyl acetate, 25 ml of a saturated aqueous sodium chloride solution and 25 ml of a saturated aqueous sodium bicarbonate solution was added- The organic layer was separated, dried over anhydrous magnesium sulfate and partially concentrated under vacuum. The residue was stirred at room temperature and a solid began to precipitate out of solution. The solid was collected by vacuum filtration to provide 180 mg of the title compound.
Analysis calculated for $C_{23}H_{29}N_3O_8$
Theory: C, 59.23; H, 4.32; N, 9.01;
Found: C, 59.45, H, 4.55; N, 9.02.

EXAMPLE 7

Synthesis of 7-[[(phenoxymethyl)carbonyl]amino]-3-hydroxy-8-oxo-1-azabicyclo[4.2.01oct-2-ene-2-carboxylic acid (4-nitrophenyl)methyl ester A. Using Sodium t-butoxide as Base A 0.67 g (9 mmol) sample of t-butanol was dissolved in 8 ml of dry tetrahydrofuran at −10° C. The solution was then treated with 0.36 g (9 mmol) of NaH and allowed to warm to room temperature and finally heated to reflux. The reaction mixture was then cooled to −74° C. and treated with a 1.00 g (o.78 mmol) sample of cis-3-[[(phenoxymethyl)carbonyl]amino]-1-(2-(4-nitrophenyl)methoxy-2-oxoethyl]-4-azetidin-2-one propanoic acid phenyl ester. The reaction was then quenched after a short time with 100 ml of 1N HCl and extracted with 100 ml of $CH_2Cl_2$. The organic phase was then dried over anhydrous $Na_2SO_4$, filtered, concentrated in vacuo, and crystallized from methyl-t-butyl ether to provide 0.63 g of the title compound as an off-white solid. (yield=75.7%)
mp =149°−152° C.
Elemental Analysis:

| | Theoretical (%) | Found (%) |
|---|---|---|
| C: | 59.1 | 59.07 |
| H: | 4.53 | 4.58 |
| N: | 8.99 | 8.97 |

B. Using sodium t-pentoxide as base

A 14.72 g (133.69 mmol) sample of sodium t-pentoxide was dissolved in 70 ml of dry tetrahydrofuran and cooled to −70° C. The solution was then treated with a 15.0g (20.74 mmol) sample of cis-3-[[(phenoxymethyl)-carbonyl]amino]-1-(2-(4-nitrophenyl)methoxy-2-oxoethyl]-4-azetidin-2-one propanoic acid phenyl ester and the reaction maintained below −50° C. for 35 minutes. The reaction mixture was quenched with 150 mmol of 1N HCl and with 8.0 ml H$_2$O. The mixture was then warmed to −20° C. and treated with 70 ml of saturated NaCl solution. The reaction mixture was then extracted with 150 ml of CH$_2$Cl$_2$. The organic phase was then dried over anhydrous MgSO$_4$, filtered and concentrated in vacuo.

Crystallization from t-butyl methylether afforded 11.01 g (88% yield) of the title compound.

mp=160°–162° C.
Elemental Analysis:

|   | Theoretical (%) | Found (%) |
| --- | --- | --- |
| C: | 59.1 | 59.05 |
| H: | 4.53 | 4.79 |
| N: | 8.99 | 9.15 |

Mass Spectrum (FD) m/e=467

We claim:

1. A process for preparing a compound of the formula

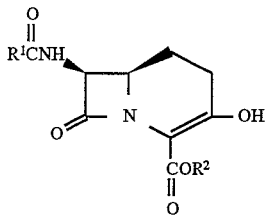

wherein $R^1$ is $C_1$–$C_6$ alkyl; a phenyl group

wherein a and a' independently are hydrogen, $C_1$–$C_4$ alkyl, $C_1$–$C_4$ alkoxy or halogen; a group represented by the formula

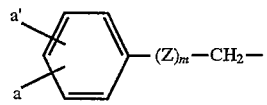

wherein z is O or S, m is 0 or 1, and a and a' have the same meanings as defined above; or $R^1$ is $R^{1''}$ O wherein $R^{1''}$ represents $C_1$–$C_4$ alkyl, $C_5$–$C_7$ cycloalkyl, benzyl, nitrobenzyl, methoxybenzyl, or halobenzyl; and $R^2$ is 4-nitrobenzyl, comprising reacting a compound of the formula

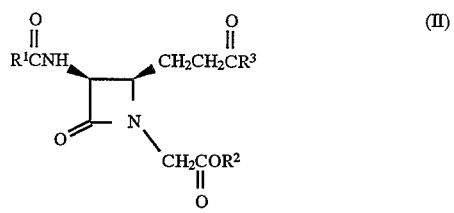

wherein $R^1$ and $R^2$ are as defined above and $R^3$ is a leaving group of the formula -$OR^4$, wherein $R^4$ is $C_1$–$C_6$ alkyl, $C_2$–$C_6$ alkenyl, phenyl, or phenyl substituted with one, two, or three substituents selected from $C_1$–$C_6$ alkyl, $C_1$–$C_6$ alkoxy, $C_1$–$C_6$ alkylthio, nitro, halo, carboxy, and amido, with a lithium tertiary alkoxide at a temperature of about −25° C. to about 27° C.

2. The process of claim 1 wherein $R^4$ is phenyl or phenyl substituted with one, two, or three substituents selected from $C_1$–$C_6$ alkyl, $C_1$–$C_6$ alkoxy, $C_1$–$C_6$ alkylthio, nitro, halo, carboxy, and amido.

3. The process of claim 2 wherein $R^1$ is phenyl, benzoyloxy, benzyl, or phenoxymethyl.

4. The process of claim 2 wherein $R^1$ is phenoxymethyl and $R^4$ is phenyl.

5. The process of claim 4 wherein the lithium tertiary alkoxide is lithium t-butoxide or lithium t-pentoxide.

6. The process of claim 5 wherein the lithium tertiary alkoxide is lithium t-butoxide.

* * * * *

UNITED STATES PATENT AND TRADEMARK OFFICE
CERTIFICATE OF CORRECTION

PATENT NO. : 5,637,692
DATED : June 10, 1997
INVENTOR(S) : Aikins, et al.

It is certified that error appears in the above-identified patent and that said Letters Patent is hereby corrected as shown below:

Column 10, line 11, "3-hydroxy-8-oxo-1-azabicyclo[4.2.0[oct-2-ene-2-" should read --3-hydroxy-8-oxo-1-azabicyclo[4.2.0]oct-2-ene-2---.

Signed and Sealed this

Twenty-second Day of September, 1998

Attest:

BRUCE LEHMAN

*Attesting Officer*    *Commissioner of Patents and Trademarks*